(12) United States Patent
Kappel et al.

(10) Patent No.: US 9,510,824 B2
(45) Date of Patent: Dec. 6, 2016

(54) LOW PROFILE MEDICAL DEVICE AND RELATED METHODS OF USE

(71) Applicant: Boston Scientific Scimed, Inc., Maple Grove, MN (US)

(72) Inventors: Gary Kappel, Acton, MA (US); Doug Melanson, Natick, MA (US); Norman May, Northborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 35 days.

(21) Appl. No.: 14/149,527

(22) Filed: Jan. 7, 2014

(65) Prior Publication Data

US 2014/0194905 A1    Jul. 10, 2014

Related U.S. Application Data

(60) Provisional application No. 61/750,182, filed on Jan. 8, 2013.

(51) Int. Cl.
| | |
|---|---|
| *A61B 17/04* | (2006.01) |
| *A61B 17/062* | (2006.01) |
| *A61B 17/29* | (2006.01) |

(52) U.S. Cl.
CPC ......... *A61B 17/0483* (2013.01); *A61B 17/062* (2013.01); *A61B 17/0625* (2013.01);
(Continued)

(58) Field of Classification Search
CPC ............ A61B 17/062; A61B 2017/294; A61B 2017/2937; A61B 17/0483; A61B 2017/2939; A61B 17/0625
See application file for complete search history.

(56) References Cited

U.S. PATENT DOCUMENTS

| | | | | |
|---|---|---|---|---|
| 1,704,992 | A * | 3/1929 | Sanders | A61B 17/062 606/147 |
| 5,133,727 | A * | 7/1992 | Bales | A61B 17/29 600/562 |

(Continued)

FOREIGN PATENT DOCUMENTS

| | | |
|---|---|---|
| FR | 2 699 394 A1 | 6/1994 |
| FR | 2699394 A1 | 6/1994 |

OTHER PUBLICATIONS

International Preliminary Report on Patentability for corresponding International Application No. PCT/US2014/010520, issued on Jul. 14, 2015, (7 pages).

*Primary Examiner* — Jing Ou
(74) *Attorney, Agent, or Firm* — Bookoff McAndrews, PLLC

(57) ABSTRACT

A medical device including an elongate member having a proximal end, a distal end, and a lumen extending therebetween. The medical device may further include an end-effector disposed at the distal end of the elongate member, the end-effector may include a first arm, the first arm may have a distal end, a proximal end, and an opening configured to receive a needle therein. The medical device may also include a second arm movably connected to the first arm and configured to alternate between a closed position and an open position relative to the first arm, wherein the second arm is movably connected to the first arm at a pivot point disposed at a location closer to the distal end of the second arm than the proximal end of the second arm.

3 Claims, 5 Drawing Sheets

(52) U.S. Cl.
CPC . *A61B 2017/294* (2013.01); *A61B 2017/2937* (2013.01); *A61B 2017/2939* (2013.01)

(56) References Cited

U.S. PATENT DOCUMENTS

| | | | | |
|---|---|---|---|---|
| 5,275,613 | A * | 1/1994 | Haber | A61B 17/29 606/139 |
| 5,304,185 | A | 4/1994 | Taylor | |
| 5,601,575 | A | 2/1997 | Measamer et al. | |
| 5,700,276 | A * | 12/1997 | Benecke | A61B 17/1608 606/206 |
| 5,951,587 | A * | 9/1999 | Qureshi | A61B 17/062 606/144 |
| 7,211,099 | B2 * | 5/2007 | Lang | A61B 17/1608 606/206 |
| 7,470,278 | B2 * | 12/2008 | Frank | A61B 17/062 606/208 |
| 2005/0043758 | A1 * | 2/2005 | Golden | A61B 10/06 606/206 |
| 2005/0119693 | A1 * | 6/2005 | Prestel | A61B 17/1608 606/207 |
| 2005/0125013 | A1 * | 6/2005 | Kessler | A61B 17/062 606/148 |

* cited by examiner

LOW PROFILE MEDICAL DEVICE AND RELATED METHODS OF USE

CROSS-REFERENCE TO RELATED APPLICATIONS

This application claims the benefit of priority from U.S. Provisional Application No. 61/750,182, filed on Jan. 8, 2013, the entirety of which is incorporated by reference herein.

FIELD OF THE INVENTION

Embodiments of the present disclosure relate generally to medical devices and procedures. In particular, embodiments of the present disclosure relate to medical devices configured to securely grasp needles and/or sutures for manipulation within a patient's body.

BACKGROUND OF THE INVENTION

Medical procedures, for e.g., endoscopic surgery, may be generally carried out by inserting a surgical tool into a patient's body through an incision or anatomical opening (e.g., oral, vaginal, and/or anal cavities). In general, all such medical procedures that include incisions over and within a patient's tissue, aim to cause minimal tissue damage. Further, these medical procedures also aim to avoid large incisions, which are commonly needed for "open" surgeries. Regardless of the size, any incision made into a patient's tissue may be ultimately sutured through well known techniques in the art.

Suturing at a surgical site can be accomplished using a needle driver, which can be provided as an end-effector carried on an endoscopic device. Typically, surgeons employ a number of needle configurations for suturing, for e.g., during minimally invasive surgical procedures. To accomplish that task, a needle driver, also referred to as a needle holder, may be a device that holds or controls surgical needles while suturing. Various types of needle drivers are available, enabling an operator to incorporate and manipulate different types of suturing techniques during a procedure. Conventional needle drivers, however, require the operator to maintain a constant minimum pressure on the needle, which is a difficult standard to meet. Unwanted needle movement may cause damage to surrounding tissues.

The art has therefore sought to reduce the size of end-effector devices, with concomitantly reduced complexity, without sacrificing actuation capability and gripping force. The primary requirement, however, remains the ability to grip a needle or an end of a suture securely while performing suturing and other tasks.

Thus, the need remains for precision needle drivers, which are able to optimize grip and control during various surgical procedures.

SUMMARY OF THE INVENTION

Embodiments of this disclosure relate generally to medical devices and procedures. In particular, embodiments of the present disclosure relate to a medical device having end-effectors that can be used to grasp, drive, and control surgical needles, sutures, and the like.

In one embodiment, a medical device may an elongate member having a proximal end, a distal end, and a lumen extending therebetween. The medical device may further include an end-effector disposed at the distal end of the elongate member, the end-effector may include a first arm, the first arm may have a distal end, a proximal end, and an opening configured to receive a needle therein. The medical device may also include a second arm movably connected to the first arm and configured to alternate between a closed position and an open position relative to the first arm, wherein the second arm is movably connected to the first arm at a pivot point disposed at a location closer to the distal end of the second arm than the proximal end of the second arm.

Various embodiments of the medical device may include one or more of the following features: the first arm may define a mounting area, and, when in the closed position, a substantial entirety of the second arm may be configured to be received within the mounting area; a distal end of the second arm may be configured to substantially close the opening in the first arm when the second arm is in the closed position; the second arm may include a grasping portion that cooperates with the opening of the first arm in the closed position; the first arm may include a longitudinal slot defined therein; in the closed position, a portion of the second arm may be configured to extend through the longitudinal slot; a portion of a periphery of the opening may include an elastomeric cover; an actuation member may be operably secured to a proximal end of the first arm, wherein the actuation member may be slidably disposed on a roller sleeve bearing; a width of the first arm is larger than a width of the second arm; and the actuation member may be a pull wire, and wherein an elastic member may be operably coupled to the actuation member to prevent buckling of the pull wire.

In another embodiment, a driver may include an elongate member having a proximal end, a distal end, and a lumen extending therebetween. The driver may also include an end-effector disposed at the distal end of the elongate member, the end-effector including a first arm, the first arm having a distal end, a proximal end, and an opening configured to receive a needle therein. The driver may also include a second arm pivotably connected to the first arm, the second arm configured to alternate between a closed position and an open position relative to the first arm, wherein in the closed position, a substantial entirety of the second arm is configured to be received within a mounting area defined by the first arm.

Various embodiments of the driver may include one or more of the following features: a distal end of the second arm may be configured to substantially close the opening in the first arm when the second arm is in the closed position; the second arm may include a grasping portion that complements the opening of the first arm in the closed position; the first arm may include a first longitudinal slot defined therein; in the closed position, a portion of the second arm may be configured to extend through the first longitudinal slot; a portion of a periphery of the opening may include an elastomeric cover; one of a length and a width of the first arm may be greater than a respective length and width of the second arm; an actuation member may be operably coupled to a proximal end of the first arm, wherein the actuation member may be slidably disposed on a roller sleeve bearing; and a second longitudinal slot may be defined by the first arm, wherein the second longitudinal slot may be disposed opposite the first longitudinal slot.

In a further embodiment, an end-effector may be connected to a distal end of an elongate member, the elongate member may have a proximal end, and a lumen extending between the proximal end and the distal end. The end-effector may include a first arm having a distal end, a proximal end, and an opening configured to receive one of a needle and a suture, wherein the first arm may include a longitudinal slot defined therein, a second arm movably coupled to the first arm and configured to alternate between a closed position and an open position relative to the first arm, wherein a width of the second arm is smaller than a width of the first arm, a grasping portion disposed on the second arm that cooperates with the opening of the first arm in the closed position to retain the one of a needle and a suture, a pull cable extending between a proximal end of the second arm and the proximal end of the elongate member, wherein the first arm defines a mounting area, and, when in the closed position, a substantial entirety of the second arm is configured to be received within the mounting area and a portion of the second arm is configured to extend through the slot.

In one embodiment, the flexible pull member is configured to deflect about a portion of the end-effector.

In one embodiment, a largest width of the first arm is larger than a largest width of the second arm.

In one embodiment, a largest width of the first arm along a second axis normal to the pivot axis is larger than a largest width of the second arm along the second axis.

In one embodiment, the flexible pull member is configured to deflect about the bearing, and extends distal of the bearing by a first length and in a first direction in the closed position, and by a second length in a second direction in the open position, the second length being greater than the first length and the first direction being offset from the second direction.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the disclosure and together with the description, serve to explain the principles of the disclosure.

DESCRIPTION OF THE EMBODIMENTS

Reference will now be made in detail to embodiments of the disclosure, an example of which is illustrated in the accompanying drawings. Wherever possible, the same reference numbers will be used throughout the drawings to refer to the same or like parts.

The present disclosure provides an improved needle driver having an end-effector with one or more features to optimize grip and control of the needle and/or suture. A medical device including the needle driver having an end-effector and a number of associated needles for use with the needle driver is disclosed herein. The needle driver may include an elongate member having a proximal end, a distal end, and a lumen extending therebetween. The elongate member may further include an end-effector disposed at its distal end, forming a jaw-like structure having a first arm and a second arm, with the second arm pivotally connected to move between open and closed configurations. Here, the pivotal connection is actuated by a pull cable connected to a proximal portion of the second arm, extending through the lumen to a compatible actuating unit. Various configurations of end-effector actuation, structure, and function are described in the embodiments of the disclosure. Further, as used in this disclosure, "distal" refers to a position or direction further from an user, and "proximal" refers to a position or direction opposite "distal" and closer to the user.

More particularly, the present disclosure provides a medical device including a needle driver having an end-effector for gripping and controlling a needle and/or suture during minimally invasive procedures. In addition, because the end-effector is not limited to grasping a suturing needle, the end-effector of the present disclosure is also useful for securely holding and manipulating tissues or other tools as may seem appropriate to a user well experienced in the art. In particular, the medical device of the present disclosure may provide a relatively high clamping or grasping force on the needle. This may allow for tighter grip of the needle during a procedure, reduced needle slippage, and may improve suturing by requiring less time, improving needle driving ability and improving accuracy of needle deployment.

Exemplary Embodiments

Figure 1A:
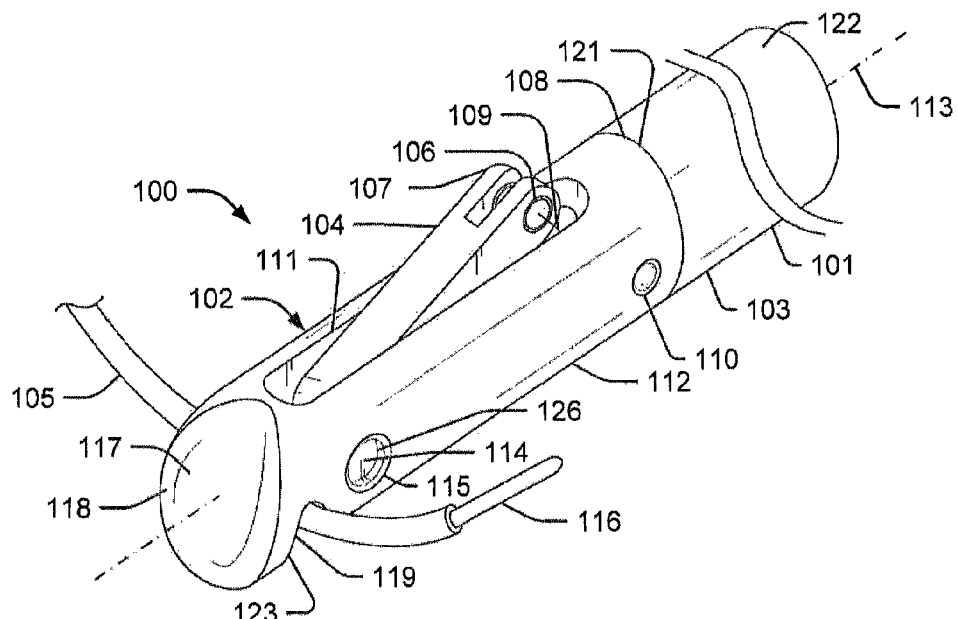
FIG. 1A is an isometric top view of a needle driver, according to an embodiment of the present disclosure.

According to an embodiment of the present disclosure, FIG. 1A is a top isometric view of an exemplary medical needle driver 100. The needle driver 100 may include an elongate member 101, having an end-effector 102. A proximal end 108 of the end-effector may be removably secured to a distal end 103 of the elongate member 101. Such connections may be achieved by any suitable means known in the art, including, e.g., a snap-fit or by crimping the distal end 103 of the elongate member 101 about the proximal end 108 of end-effector 102. Further, the elongate member 101 may include a lumen 124 (shown in FIG. 2B) extending within and along the length of the elongate member 101 from the distal end 103 to a proximal end 122 of the elongate member 101. In addition, a mounting area 208 (illustrated in FIG. 2B) may be configured within the end-effector 102.

Figure 1B:
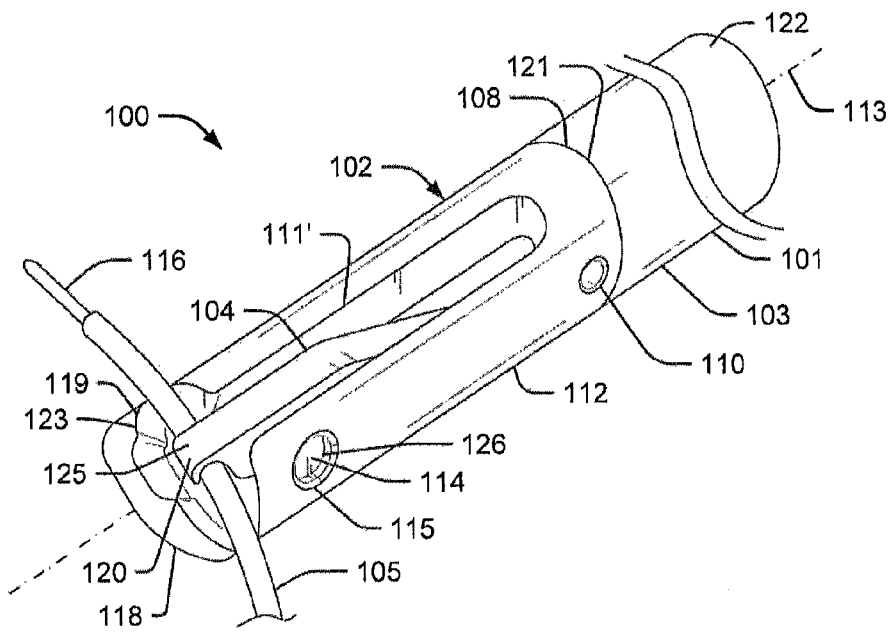
FIG. 1B is an isometric bottom view of the needle driver depicted in FIG. 1A.

The end-effector 102 may include a first arm 112 having proximal and distal ends 121 and 118, respectively, as well as a second arm 104, likewise including a proximal and distal ends 107 and 125 (shown in FIG. 1B). According to the depicted embodiment, the first arm 112 may be configured to include a generally cylindrical shape, extending along the length of the first arm 112, with the mounting area 208 configured and defined therein. A flange 117 may generally extend distally from first arm 112. Further, a cylindrical aperture 110, passing diametrically through the first arm 112, may be disposed closer to the proximal end 121 than the distal end 118 of the first arm 112. Similarly, a cylindrically shaped pivot aperture 115, also passing diametrically through the first arm 112, may be disposed closer to the distal end 118 than the proximal end 121 of the first arm 112. In particular, the aperture 115 may be configured to include a pivot point 114, which may enable the second arm 104 (described later) to pivot in relation to the first arm 112, when assembled appropriately at the pivot aperture 115. Particularly, the pivot point 114 may include a pivot pin 126 that may enable the two arms 104 and 112 to maintain a movable connection, and, more particularly, a pivotal connection in relation to each other. A longitudinal slot 111, parallel to an axis 113 of the elongate member 101, may be provided in the first arm 112 to receive the second arm 104 during its pivotal movements. Similarly, a slot 111' (shown in FIG. 16) disposed diametrically opposite of the slot 111 may be configured on the first arm 112 as well. In addition, the cylindrical aperture 110 may be configured to support a friction reducing member, such as a roller bearing 204 (depicted in FIG. 2B).

Furthermore, an opening 119 may be disposed on the first arm 112, and may be configured to accept a needle assembly, such as the needle assembly 105 that includes a needle portion 116. Here, the needle assembly 105 may include a sheath (not shown) that retains and locks the needle portion 116 therein, while the needle portion 116 forms the section that leads the needle assembly 105 during a suturing procedure, assisting in suturing a tissue. The opening 119, as disclosed, may be a needle receiving notch that enables an appropriate accommodation of the needle assembly 105 during an application of the needle driver 100. In some embodiments, the opening 119 may include grooves, patches, slots, etc., to grip the needle assembly 105 positively during a surgical procedure. The opening 119 may extend substantially perpendicular to axis 113 of the elongate member 101, and as part of the atraumatic features, the opening 119 may include rounded corners and edges throughout. In particular, the opening 119 may include a wider mouth portion 123 to facilitate guiding the needle assembly 105 into the opening 119. The first arm 112 and the second arm 104, in general, may include rounded corners and edges all throughout their profile as well.

The second arm 104 may be smaller in dimensions than the first arm 112, and may be linearly shaped while having the ability to be entirely disposed within the first arm 112 during certain applications of the end-effector 102. As discussed above, the second arm 104 may be movably or pivotally connected to the first arm 112, with the pivot point 114 positioned closer to the distal end 125 of the second arm 104 than to the proximal end 107. At its proximal end 107, the second arm 104, may include a swivel crimp 106 to flexibly accept a pull cable 109 extending between the proximal end 107 of the second arm and the proximal end 122 of the elongate member 101.

FIG. 1B is a bottom isometric view of the needle driver 100. As shown, the end-effector 102 may include a grasping portion, referred to as a needle grasping portion 120, disposed at a distal end 125 of the second arm 104. Particularly, the needle grasping portion 120 may be a jaw-like structure and may include configurations cooperating with the configurations of the opening 119 to accept a needle assembly, such as the needle assembly 105. Accordingly, the needle grasping portion 120 may include grooves, patches, slots, etc., similar to ones discussed for the opening 119. The slot 111', as noted above, may be adapted to accommodate the second arm 104 during a pivotal motion of the second arm 104 in relation to the first arm 112. It will therefore be understood from the depicted embodiment that the second arm 104 may be configured to be accommodated within the mounting area 208 of the first arm 112 during certain stages of operation of the end-effector 102. In particular, a substantial entirety of the second arm 104 is configured to be received within the mounting area 208 defined by the first arm 112 in a closed position (Shown in FIG. 5).

The flexible connection of the swivel crimp 106 to the pull cable 109 may enable a positive engagement of the pull cable 109 to the swivel crimp 106, particularly during pivotal motions of the second arm 104. The other end of the pull cable 109 may be connected at the proximal end 122 of the elongate member 101, or may be connected to any other desirable and compatible location within the assembly of the needle driver 100 from where operation of the pull cable 109 may be possible. More particularly, the pull cable 109 in turn may be adapted to be supported via the roller bearing 204 during pivotal movements of the second arm 104 (discussed later).

It will be understood that the described movements of the second arm 104 relative to the first arm 112 may include configurations other than the pivotal movements described, and may thus include transverse, linear, or slidable movements as well. For example, a relative linear movement between the two arms 112 and 104, disposed on a common axis, can include needle receiving notches or needle clamping measures to be configured on either or both of the arms 112 and 104, where the arms 112 and 104 may be springably and linearly connected to each other. Controlling one arm relative to the other, through a pull cable or the like, may configure an open position and a closed position between the two, enabling grasping of a needle in the closed position, through the needle receiving notches, and release of the needle while in the open position. Techniques and measures to configure such arrangements and their related method of manufacturing are well known to the skilled in the art and will not be discussed further. The disclosed pivotal movements, therefore, do not limit the aspects of the present disclosure in any way.

The arms 104 and 112 may be made of a biocompatible material, which may be atraumatic to tissue and the like may include materials such as nitinol, metals, plastics, ceramics, and so forth. The arms 104 and 112 may also include biocompatible coatings that may impart nonirritant and atraumatic characteristics to the end-effector 102 when employed to interact with a human tissue. Particularly, such coatings may be may be drug eluting as well. Suitable coatings may include, for example, anticoagulants, anesthetic, etc. Further, manufacturing the end-effector 102 may be accomplished using known techniques in the art, such as through injection molding, etc.

Alternatively, the arms 112 and 104 may carry shapes, sizes, and designs, other than the ones depicted, and such may be incorporated and applied by those skilled in the art to accomplish a related operation.

Figure 2A:
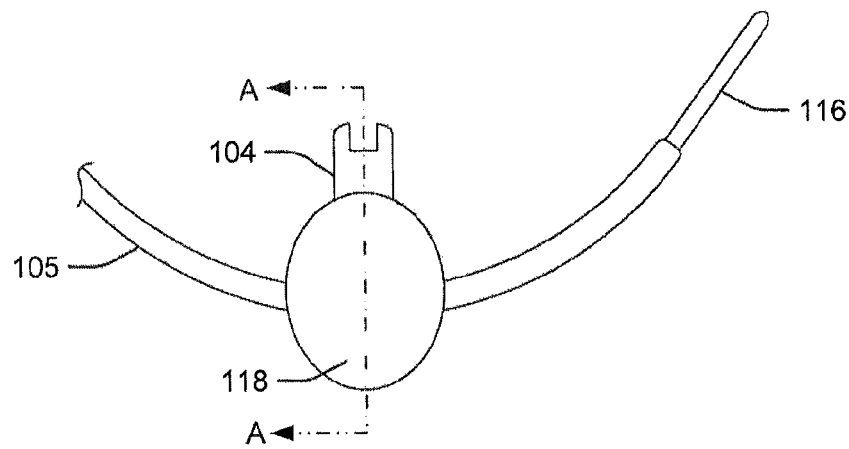
FIG. 2A is a front view of the needle driver of FIG. 1A.
Figure 2B:
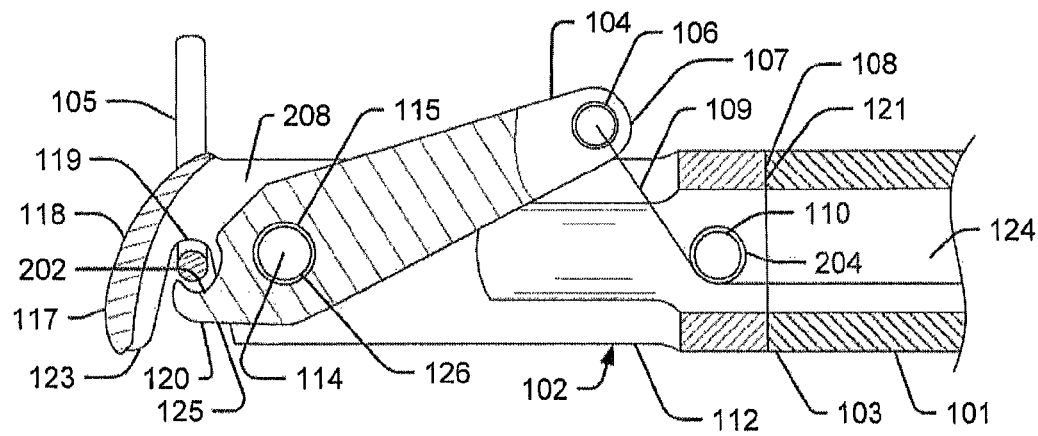
FIG. 2B is a sectional view of the needle driver shown in FIG. 1A.

FIG. 2A depicts a front view of the medical needle driver 100 and FIG. 2B is a side cross-sectional view of the needle driver 100. Herein, the mounting area 208 within the first arm 112 may form an enclosure within which the second arm 104 may rotate on the pivot point 114. As stated above, pivotal movements of the second arm 104, relative to the first arm 112, may further be enhanced through the slots 111 and 111', allowing the second arm 104 to swing beyond the confines of the mounting area 208 when desired. The needle grasping portion 120 may include an inner face 202 to interact and accept the needle assembly 105 as well.

Figure 4:
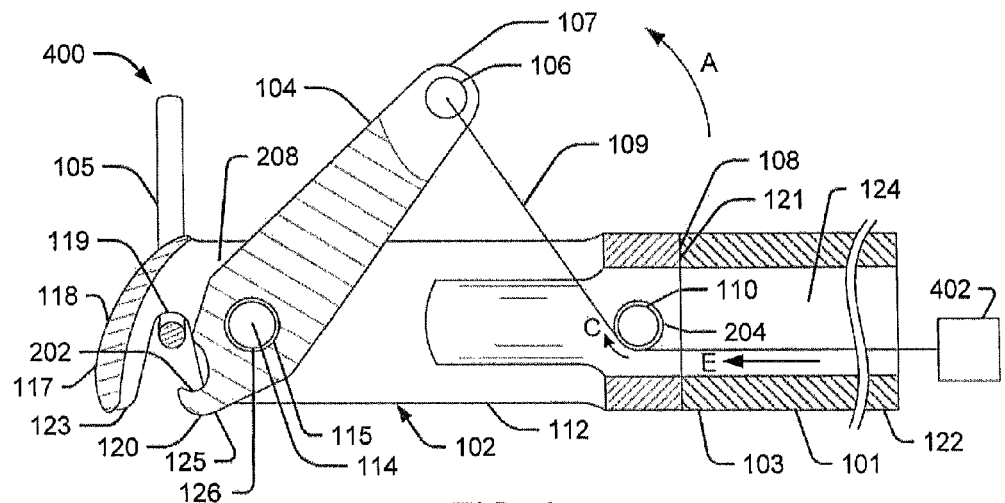
FIG. 4 is a sectional view of the needle driver of FIG. 1A in an open position.
Figure 5:
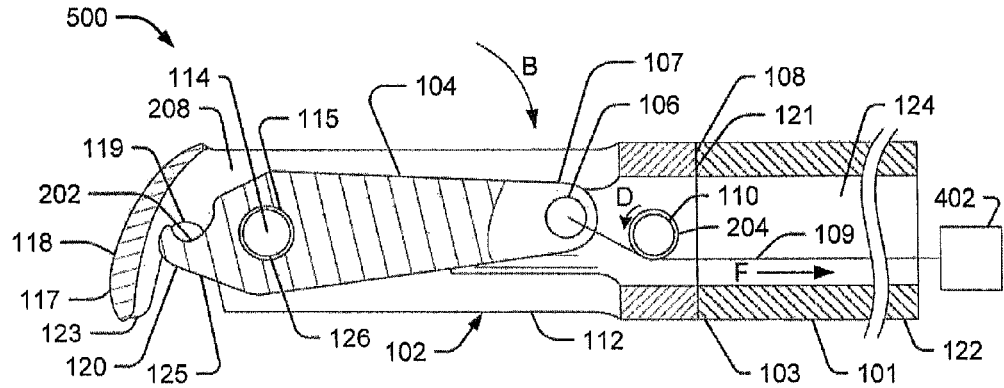
FIG. 5 is a sectional view of the needle driver of FIG. 1A in a closed position.

Further, the roller bearing 204, which may include grooves to accept the pull cable 109, may rotate according to the arrows C and D, depicted in FIG. 4 and FIG. 5. In some embodiments, however, roller bearing 204 may not rotate, allowing pull cable 109 to glide across a surface of the roller bearing 204. The arrows E and F depict a corresponding movement of the pull cable 109 according to the arrows C and D, respectively. The application of the roller bearing 204 being well known in the art will not be discussed further.

Figure 3A:
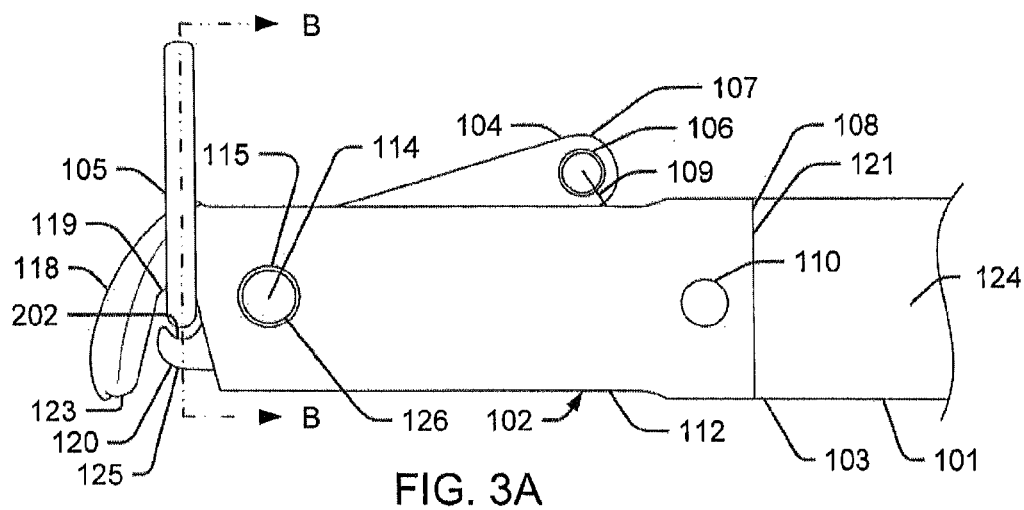
FIG. 3A is a left side view of the needle driver of FIG. 1A.
Figure 3B:
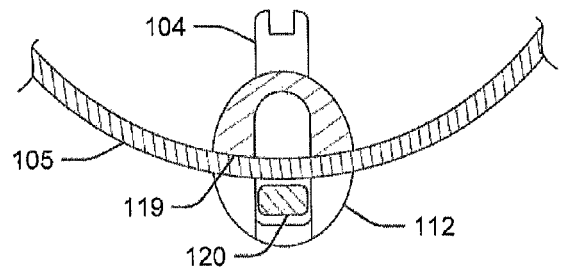
FIG. 3B is a sectional view of the needle driver shown in FIG. 1A.

Likewise, FIG. 3A depicts a side view of the medical needle driver 100 and FIG. 3B is a front cross-sectional view of the needle driver 100. In particular, FIG. 3B illustrates the needle assembly 105 in a partially engaged state with the end-effector 102. The partial engaged state is due to a partially closed position of the second arm 104 in relation to the first arm 112. It will be understood that in a completely closed position 500 (as shown in FIG. 5) of the first arm 112 relative to the second arm 104, the needle grasping portion 120 may grasp the needle assembly 105 in a manner such that a positive engagement between the needle assembly 105 and the end-effector 102 is established. It is contemplated that portions of the first and second arms 104, 112 and, in particular, the respective opening 119 and needle grasping portion 120, may be knurled, include one or more ridges, and/or include surface texturing to improve the frictional engagement with the needle.

Therefore, the second arm 104, having a needle grasping portion 120 and adapted to move pivotally to the first arm 112 via the pivot point 114, is configured to alternate between an open position 400 (shown in FIG. 5) and the discussed closed position 500 in relation to the first arm 112. Moreover, the stated closed position 500 of the end-effector 102 is described further below.

The open position 400 may be configured in such a way that the needle grasping portion 120 moves away from the opening 119 of the first arm 112, such as illustrated in FIG. 4. In such a configuration, it will be understood that the end-effector 102 lies in a state to accept the needle assembly 105. Moreover, the figure also depicts the second arm 104 to have pivoted well beyond the confines of the first arm 112. The arrow A corresponds to the pivotal movement of the second arm 104 relative to the first arm 112 in the stated open position 400.

Further, while being in the closed position 500, the distal end 125 of the second arm 104, adapted to include the needle grasping portion 120, is enabled to complement the opening 119, thereby allowing the end-effector 102 to grasp the needle assembly 105. The closed position 500 may be configured in such a way that the needle grasping portion 120 complements and lies in registration with the opening 119 of the first arm 112, such as illustrated in FIG. 5. It may be noted that the second arm 104 may not pivot outside the first arm 112, but rather may remain totally within the first arm 112 while being in the closed position 500. In addition, the arrow B corresponds to the position of the second arm 104 relative to the first arm 112 as depicted in the FIG. 5.

Through the above described embodiments of the present disclosure, it will be understood that at all times the first arm 112 may remain stationery to the elongate member 101, while variations occur in the position of the second arm 104, which moves pivotally relative to the first arm 112.

In optional embodiments, the second arm 104 may omit the needle grasping portion 120, and the function of grasping the needle assembly 105 may be accomplished solely by the opening 119, when both the arms 112 and 104 are in the closed position 500. It will be understood that in such a configuration, the shape of the opening 119 must be configured to at least partially accommodate the needle assembly 105.

More particularly, the jaw-like structure of needle grasping portion 120 allows needle assemblies, such as the needle assembly 105, to be held via the end-effector 102, allowing the needle assembly 105 to establish a positive engagement with the needle driver 100.

Alternatively, grooves, slots, notches, etc. (not shown), could be incorporated into the opening 119, the needle grasping portion 120, or both, to establish a positive handling of the needle assembly 105 while being in the closed position 500.

Further embodiments, illustrated in FIG. 4 and FIG. 5 schematically represent a compatible actuating unit 402 connected to the pull cable 109. The movements of the pull cable 109, depicted by arrows E and F, may be controllable through the actuating unit 402, or manually through a handle, as part of the actuating unit 402, available at the proximal end 122 of the elongate member 101. Accordingly, the actuating unit 402, being connected to the pull cable 109, may be operated either manually or electronically to accomplish operations resulting in the open position 400 and closed position 500. The pull cable 109 may include a spring or other structural element to prevent buckling when moving away from the actuating unit 402, as depicted by arrow E.

While in application therefore, the end-effector 102 being a medical device, may be used to hold, control, and drive, a needle assembly, such as the needle assembly 105 during a surgical process within a patient's body. In some embodiments, the end-effector 102 may be configured to securely grasp a suture or a staple. The closer positioning of the pivot point 114 to the distal end 125 than the proximal end 107 of the second arm 104 enables sufficient clamping torque to be applied for grasping the needle assembly 105. Along with the end-effector 102, certain embodiments may include the disposal of an imaging device at the distal end 103 of the elongate member 101, enabling visual feedback to be obtained to a user at the proximal end 122 of the elongate member 101. The actuating unit 402, in particular, may be configured to operate all such imaging functionalities as well.

Figure 6:
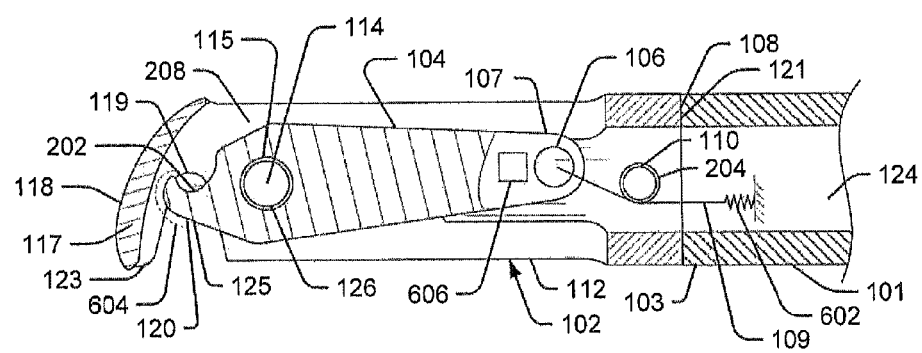
FIG. 6 depicts a sectional view of the needle driver of FIG. 1A.

Certain embodiments of the present disclosure may enable the needle grasping portion 120 to include an elastomeric member or coating, such as the member 604, shown in FIG. 6, formed over the jaw-like structure of the needle grasping portion 120, as shown. Particularly, the member 604 may be applied to enable the end-effector 102 to grasp the needle assembly 105 with sufficient grip. Similar gripping members can be configured to be formed within the opening 119 as well, and related methods of manufacturing being well known to the skilled in the art, will not be discussed further. It is contemplated that the elastomeric member or coating may improve the frictional grip of the needle. Optionally, the member 604 may either be disposed as a removable unit or may be permanently attached to either the needle grasping portion 120, opening 119, or both. It will be understood that compatible materials other than the member 604 may be employed alternatively, and thus this embodiment of enhancing grip to a needle assembly may not be limiting in any way.

Further embodiments, as depicted in FIG. 6, may enable the pull cable 109 to include a resilient member, such as a compression spring 602. That device may apply a spring force to pull cable 109, urging the second arm 104 into a closed position. In particular, certain embodiments may include the spring force provided by either or both the pull cable 109 and the compression spring 602 to urge the second arm 104 to an open configuration as well. It may be understood that spring forces being applied in such an embodiment may be applied along a linear axis of the pull cable 109 or an axis of the employed compression spring 602. Alternatively, torsion springs may be employed for urging the second arm 104 to either the closed or the open positions as well. Torsion springs, however, may transfer a spring force along a plane perpendicular to an axis of the torsion spring. Measures and configurations to enable such spring forces are well known to the skilled in the art and thus will not be discussed further.

Constant tension on the pull cable 109 may prevent it from buckling during an application, the application involving mainly the pivotal movements of the second arm 104 relative to the first arm 112, causing the pull cable 109 to move in the linear directions, as depicted through the arrows E and F. Alternative embodiments may replace compression spring 602 with a torsion spring (not shown) configured and positioned along an axis of the roller bearing 204, at the cylindrical aperture 110, providing adequate resilience to the lateral movements of the pull cable 109 and consequently preventing the pull cable 109 from buckling. Similarly, a torsion spring may be disposed at the swivel crimp 106 or at the pivot point 114 as well, to prevent the condition of buckling. In some embodiments, a stretchable pull cable could be used in place of the pull cable 109.

Markings, such as colored marker 606, may be disposed on the second arm 104 on either sides, close to the proximal end 107 of the second arm 104, as shown, to enable an operator to visually confirm an open position or a closed position of the end-effector 102. Correspondingly, compatible markers (not shown) could be disposed on the first arm 112 as well, likewise visually enabling an operator to confirm an open or closed condition. Alternatively, the marker 606 may include patterns, designs, and the like, that when superimposed over another compatible marker may visually differentiate between a closed position and an open position. Further, the indication of a closed or open position may include the marker 606 to be disposed on other convenient locations of the end-effector 102 as well. In addition, audio and/or tactile confirmations may be provided as well.

In some embodiments, the opening 119 and the needle grasping portion 120 can be configured to perform tasks beyond grasping needles. For example, the peripheries of both elements could be beveled to provide sharpened edges, allowing the medical device to cut tissue where needed. Alternatively, both elements could be provided with electrically isolated portions, which could then be provided with electric power to perform electrocautery. Related electrical connections may be provided through cabled connections passing through dedicated channels configured within the elongate member 101.

Figure 7:
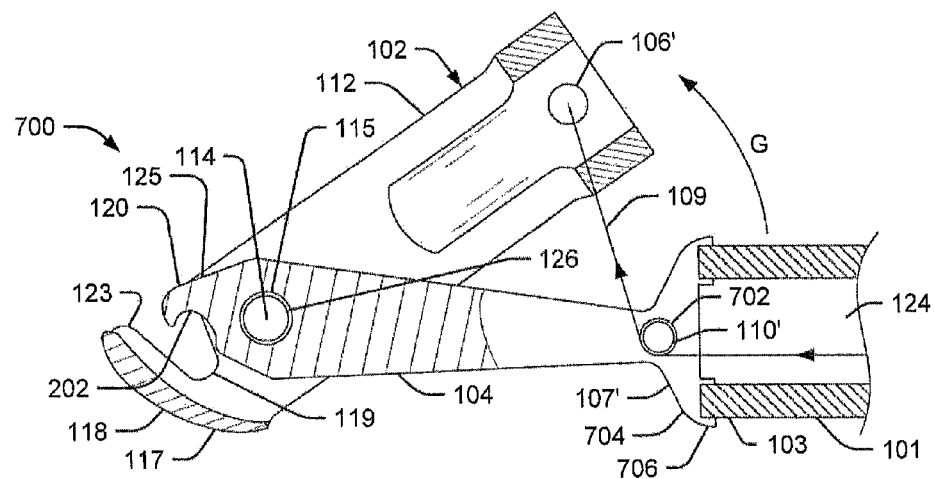
FIG. 7 depicts another embodiment of a needle driver, according to the present disclosure.

In further embodiments, the operation of the end-effector 102 may be reversed, so the first arm 112 pivots relative to the second arm 104, while the second arm 104 remains stationery relative to the elongate member 101. An embodiment 700 of such a pivotal movement of the first arm 112 in relation to the second arm 104 is depicted through the arrow G in the FIG. 7. Particularly, a bearing 702, similar to the roller bearing 204, may be employed at a swivel point 110', which is positioned closer to a proximal end 107' of the second arm 104, providing support to the employed pull cable 109. The proximal end 107' may include a trapezoidal fin-like region forming a clamp structure 704 to engage the distal end 103 of the elongate member 101 and the second arm 104 together through a snap-section 706. A swivel crimp 106', flexibly engaging the pull cable 109 and similar to the swivel crimp 106 discussed earlier, may be configured on the first arm 112, positioned in a fashion similar to the positioning of the aperture 110.

Figure 8:
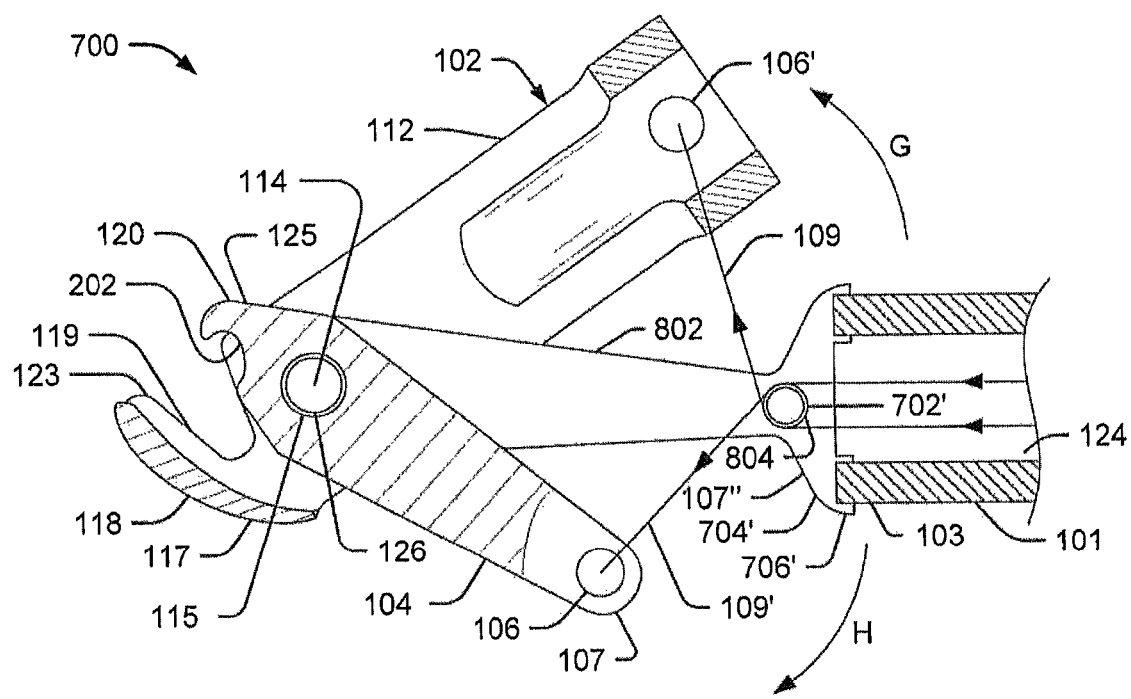
FIG. 8 depicts yet another embodiment of a needle driver, according to the present disclosure.

In some embodiments, both the first arm 112 and the second arm 104 may be configured to pivot relative to each other and the elongate member 101, as shown in FIG. 8. In such an embodiment, a third arm 802 may be configured to remain stationery to the elongate member 101, while providing a common pivot point, such as the pivot point 114 for both the first arm 112 and the second arm 104, to pivot about the third arm 802. Further, a clamp structure 704', similar to the clamp structure 704, disposed at a proximal end 107" of the third arm 802 may engage the distal end 103 of the elongate member 101 through a snap-section 706', similar to the snap-section 706. Likewise, a bearing 804, along with a bearing 702', may be configured to cater to the movement of another pull cable 109'. The pull cable 109' may be configured to be connected at one end to the swivel crimp 106, while the other end of the pull cable 109' may extend to the proximal end 122 (shown in FIG. 1A) of the elongate member 101. As the first arm 112 pivots according to the arrow G, the second arm 104 may be configured to swing according to the arrow H, as shown in the figure.

Other embodiments of the present disclosure will be apparent to those skilled in the art from consideration of the specification and practice of the embodiments disclosed herein. It is intended that the specification and examples be considered as exemplary only, with a true scope and spirit of the invention being indicated by the following claims.

What is claimed is:

1. An end-effector connected to a distal end of an elongate member, the elongate member having a proximal end, and a lumen extending between the proximal end and the distal end, the end effector comprising:
   a first arm having a distal end, a proximal end, and an opening configured to receive one of a needle and a suture, wherein the first arm includes a longitudinal slot defined therein;
   a bearing coupled to the first arm;
   a second arm movably coupled to the first arm about a pivot axis and configured to alternate between a closed position and an open position relative to the first arm, wherein a largest width of the second arm along a second axis normal to the pivot axis is smaller than a largest width of the first arm along the second axis;
   a grasping portion disposed on the second arm that cooperates with the opening of the first arm in the closed position to retain the one of a needle and a suture; and
   a flexible pull member extending between a proximal end of the second arm and the proximal end of the elongate member, wherein the first arm defines a mounting area, and, when in the closed position, a substantial entirety of the second arm is configured to be received within the mounting area and a portion of the second arm is configured to extend through the longitudinal slot, wherein the flexible pull member is supported by the bearing when the second arm is moved between the closed position and the open position, is configured to deflect about the bearing, and extends distal of the bearing by a first length and in a first direction in the closed position, and by a second length in a second direction in the open position, the second length being greater than the first length and the first direction being offset from the second direction.

2. The medical device of claim 1, further including a spring coupled to the flexible pull member, wherein the spring is configured to prevent buckling of the flexible pull member.

3. The medical device of claim 2, wherein the bearing rotates as the second arm moves between the closed position and the open position.

* * * * *